(12) United States Patent
Verma et al.

(10) Patent No.: US 9,952,517 B2
(45) Date of Patent: Apr. 24, 2018

(54) METHOD OF DETERMINING DOSE, INSPECTION APPARATUS, PATTERNING DEVICE, SUBSTRATE AND DEVICE MANUFACTURING METHOD

(71) Applicant: ASML Netherlands B.V., Veldhoven (NL)

(72) Inventors: Alok Verma, Eindhoven (NL); Hugo Augustinus Joseph Cramer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 81 days.

(21) Appl. No.: 14/753,642

(22) Filed: Jun. 29, 2015

(65) Prior Publication Data

US 2016/0026096 A1    Jan. 28, 2016

(30) Foreign Application Priority Data

Jun. 30, 2014    (EP) .................................... 14174973

(51) Int. Cl.
*G03B 27/72* (2006.01)
*G03F 7/20* (2006.01)
*G01N 21/47* (2006.01)

(52) U.S. Cl.
CPC ..... *G03F 7/70558* (2013.01); *G01N 21/4738* (2013.01); *G01N 21/4785* (2013.01);
(Continued)

(58) Field of Classification Search
CPC ............. G03F 7/70558; G03F 7/70625; G03F 7/70683; G03F 7/7085; G01N 21/4785
(Continued)

(56) References Cited

U.S. PATENT DOCUMENTS 5,674,650 A    10/1997 Dirksen et al.
6,251,544 B1    6/2001 Inoue et al.
(Continued)

FOREIGN PATENT DOCUMENTS

CN    102422227 A    4/2012
EP    1 881 374 A2    1/2008
(Continued)

OTHER PUBLICATIONS

International Search Report directed to related International Patent Application No. PCT/EP2015/062778, dated Oct. 19, 2015; 2 pages.
(Continued)

*Primary Examiner* — Peter B Kim
(74) *Attorney, Agent, or Firm* — Sterne, Kessler, Goldstein & Fox P.L.L.C.

(57) ABSTRACT

A method of determining exposure dose of a lithographic apparatus used in a lithographic process on a substrate, the method comprising the steps: (a) receiving a substrate comprising first and second structures produced using the lithographic process; (b) detecting scattered radiation while illuminating the first structure with radiation to obtain a first scatterometer signal; (c) detecting scattered radiation while illuminating the second structure with radiation to obtain a second scatterometer signal; (d) using the first and second scatterometer signals to determine an exposure dose value used to produce said first and second structures wherein the first structure has a first periodic characteristic with spatial characteristics and yet at least another second periodic characteristic with spatial characteristics designed to be affected by the exposure dose and the second structure has a first periodic characteristic with spatial characteristics and yet at least another second periodic characteristic with spatial characteristics designed to be affected by the expo-
(Continued)

sure dose wherein the exposure dose affects the exposure dose affected spatial characteristics of the first and second structures in a different manner.

19 Claims, 5 Drawing Sheets

(52) U.S. Cl.
CPC ........ *G03F 7/7085* (2013.01); *G03F 7/70625* (2013.01); *G03F 7/70683* (2013.01); *G01N 2021/4735* (2013.01)

(58) Field of Classification Search
USPC .......................................................... 355/69
See application file for complete search history.

(56) References Cited

U.S. PATENT DOCUMENTS

| | | |
|---|---|---|
| 6,879,400 B2 | 4/2005 | Ausschnitt et al. |
| 7,352,453 B2 | 4/2008 | Mieher et al. |
| 7,439,001 B2 | 10/2008 | Ausschnitt et al. |
| 7,667,842 B2 | 2/2010 | Schulz |
| 7,700,247 B2 | 4/2010 | Ausschnitt |
| 7,771,905 B2 | 8/2010 | Sentoku et al. |
| 7,916,284 B2 | 3/2011 | Dusa et al. |
| 8,830,447 B2 | 9/2014 | Den Boef et al. |
| 8,994,944 B2 | 3/2015 | Cramer et al. |
| 2004/0058256 A1 | 3/2004 | Fujisawa et al. |
| 2004/0190008 A1* | 9/2004 | Mieher ............... G01N 21/956 356/625 |
| 2004/0233445 A1 | 11/2004 | Littau et al. |
| 2005/0018164 A1 | 1/2005 | Hansen |
| 2005/0173634 A1 | 8/2005 | Wong et al. |
| 2006/0146310 A1 | 7/2006 | De Kruif et al. |
| 2006/0170899 A1 | 8/2006 | De Kruif et al. |
| 2007/0050749 A1 | 3/2007 | Ye et al. |
| 2008/0018874 A1 | 1/2008 | Dusa et al. |
| 2010/0075238 A1 | 3/2010 | Fonseca et al. |
| 2010/0201963 A1 | 8/2010 | Cramer et al. |
| 2010/0221659 A1 | 9/2010 | Ebata et al. |
| 2010/0328636 A1 | 12/2010 | Quaedackers et al. |
| 2011/0027704 A1 | 2/2011 | Cramer et al. |
| 2011/0043791 A1 | 2/2011 | Smilde et al. |
| 2011/0109888 A1 | 5/2011 | Van Der Schaar et al. |
| 2011/0249247 A1 | 10/2011 | Cramer et al. |
| 2011/0295555 A1 | 12/2011 | Meessen et al. |
| 2012/0044472 A1 | 2/2012 | Den Boef et al. |
| 2012/0123581 A1 | 5/2012 | Smilde et al. |
| 2012/0206703 A1 | 8/2012 | Bhattacharyya et al. |
| 2013/0217154 A1 | 8/2013 | Fukazawa et al. |
| 2014/0307256 A1 | 10/2014 | Amir |
| 2015/0293458 A1* | 10/2015 | Vanoppen ........... G03F 7/70558 355/53 |
| 2015/0308966 A1 | 10/2015 | Grootjans et al. |
| 2015/0338749 A1 | 11/2015 | Hinnen et al. |
| 2016/0026096 A1 | 1/2016 | Verma et al. |
| 2016/0061589 A1 | 3/2016 | Bhattacharyya et al. |
| 2016/0061750 A1 | 3/2016 | Den Boef et al. |
| 2016/0116849 A1 | 4/2016 | Cramer et al. |
| 2016/0146740 A1 | 5/2016 | Lu et al. |
| 2016/0180517 A1 | 6/2016 | Fuchs et al. |
| 2016/0274456 A1 | 9/2016 | Chen et al. |
| 2016/0313654 A1 | 10/2016 | Zeng et al. |
| 2016/0363871 A1 | 12/2016 | Van Oosten et al. |
| 2016/0370710 A1 | 12/2016 | Wardenier et al. |
| 2017/0059999 A1 | 3/2017 | Van Der Schaar et al. |
| 2017/0090302 A1 | 3/2017 | Slotboom et al. |

FOREIGN PATENT DOCUMENTS

| | | |
|---|---|---|
| JP | H09-504142 A | 4/1997 |
| JP | 2010-133941 A | 6/2010 |
| WO | WO 99/45340 A1 | 9/1999 |
| WO | WO 2009/051088 A1 | 4/2009 |
| WO | WO 2009/078708 A1 | 6/2009 |
| WO | WO 2009/106279 A1 | 9/2009 |
| WO | WO 2010/012624 A1 | 2/2010 |
| WO | WO 2013/189724 A2 | 12/2013 |
| WO | WO 2012/056601 A1 | 3/2014 |
| WO | WO 2014/082938 A1 | 6/2014 |
| WO | WO 2015/153497 A1 | 10/2015 |

OTHER PUBLICATIONS

International Preliminary Report on Patentability and Written Opinion of the International Searching Authority directed to related International Patent Application No. PCT/EP2015/062778, dated Jan. 3, 2017; 8 pages.

International Search Report directed to related International. Patent Application No. PCT/EP2013/074516, dated Mar. 25, 2014; 4 pages.

International Preliminary Report on Patentability and Written Opinion of the International Searching Authority directed to related International Patent Application No. PCT/EP2013/074516, dated Jun. 2, 2015; 8 pages.

\* cited by examiner

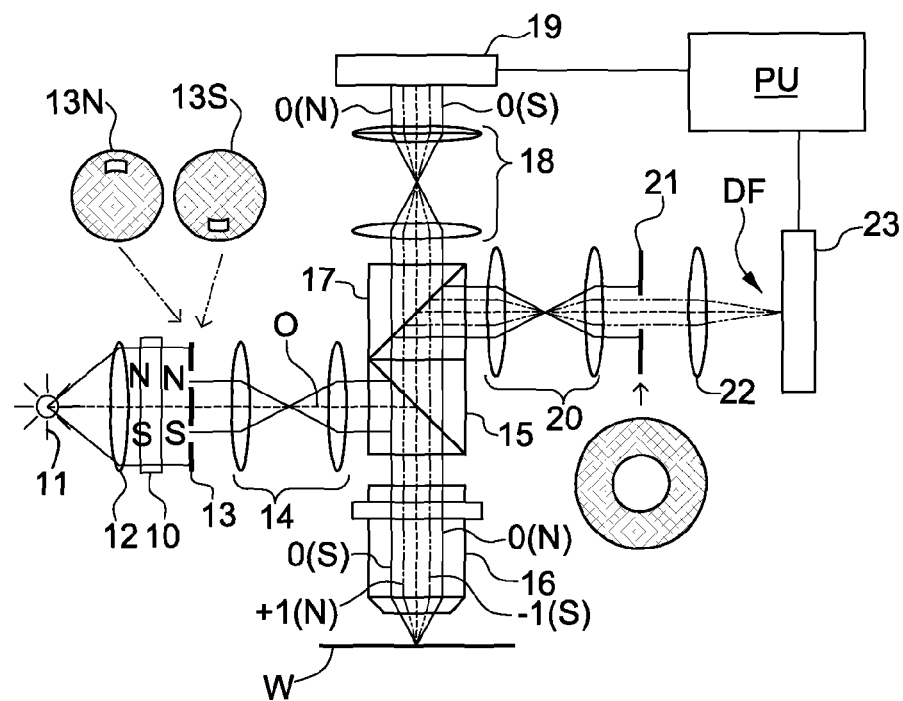
Fig. 3A
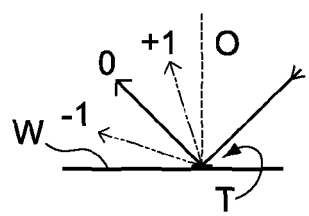
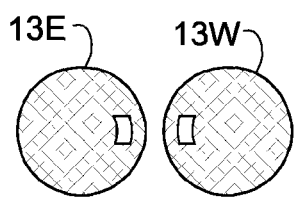
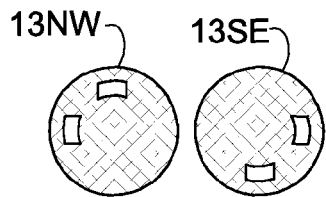
Fig. 3B　　　Fig. 3C　　　Fig. 3D

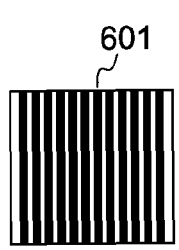
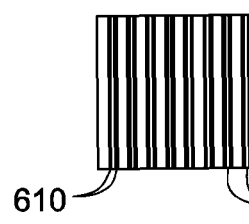
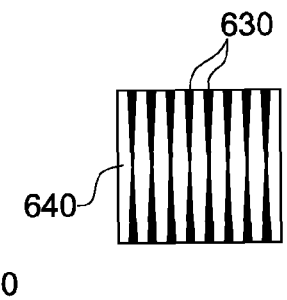
Fig. 6A    Fig. 6B    Fig. 6C
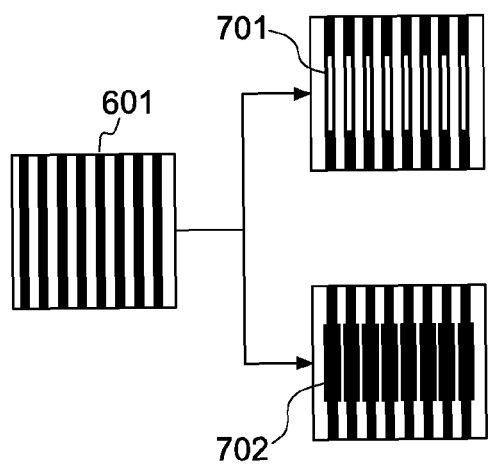
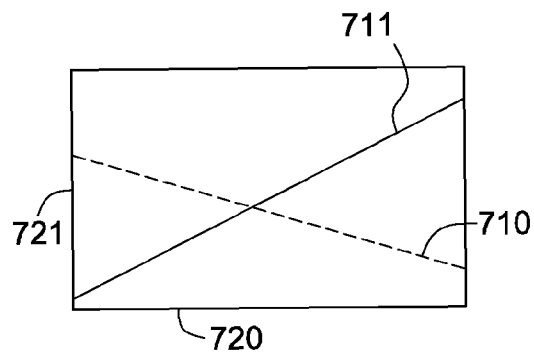
Fig. 7B
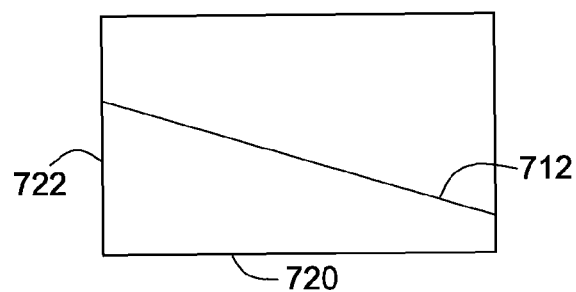
Fig. 7A
Fig. 7C

METHOD OF DETERMINING DOSE, INSPECTION APPARATUS, PATTERNING DEVICE, SUBSTRATE AND DEVICE MANUFACTURING METHOD

CROSS REFERENCE TO RELATED APPLICATIONS

This application claims benefit of EP Patent Application No. 14174973, filed on Jun. 30, 2014.

BACKGROUND

Field of the Invention

The present invention relates to methods and apparatus for determining exposure dose of a lithographic apparatus usable, for example, with pupil-plane detection or dark-field scatterometry in the manufacture of devices by lithographic techniques and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment of two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark-field scatterometry in which the zeroth order of diffraction (corresponding to a specular reflection) is blocked, and only higher orders processed.

Diffraction-based overlay using dark-field detection of the diffraction orders enables overlay measurements on smaller targets. These targets can be smaller than the illumination spot and may be surrounded by product structures on a wafer. Multiple targets can be measured in one image.

In the known metrology technique, overlay measurement results are obtained by measuring the target twice under certain conditions, while either rotating the target or changing the illumination mode or imaging mode to obtain separately the $-1^{st}$ and the $+1^{st}$ diffraction order intensities. Comparing these intensities for a given grating provides a measurement of asymmetry in the grating.

Asymmetry in a pair of stacked gratings can be used as an indicator of overlay error. Similarly, asymmetry in a focus-sensitive grating can be used as an indicator of defocus.

However, any effect that leads to an asymmetry change in the scatterometer pupil will be attributed to scanner defocus. One such effect is that of exposure dose. Exposure dose variation is difficult to measure, especially with small in-die targets.

The effective exposure dose, arising from the combination of lithographic apparatus, reticle and processing, is typically measured through line width (critical dimension, CD) of critical product structures. Inspection apparatus used for such measurements includes metrology tools such as CD-SEM (Scanning Electron Microscope) and scatterometers.

However, CD-SEM is relatively slow. Optical reconstruction using scatterometers is also a slow process. Furthermore, although scatterometers are very sensitive metrology tools, the sensitivity is to a wide range of feature parameters. Careful scatterometer setup recipe creation and optimization is needed to separate CD variations from variations in the underlying stack of materials making up the target. Moreover, scatterometry for CD measurement typically requires large targets (for example 40×40 µm).

SUMMARY

It is desirable to measure exposure dose faster than existing methods. Furthermore, it would be of great advantage if this could be applied to small target structures that can be read out with the dark-field image-based technique. Moreover, it is considered advantageous to incorporate metrology features used for exposure dose measurements in metrology features used, for example, in overlay or focus measurements, without interfering with said measurements, i.e., metrology targets which follow the design rules and, at the same time, can be embedded within metrology targets with different functionality.

According to a first aspect, there is provided a method of determining exposure dose of a lithographic apparatus used in a lithographic process on a substrate, the method comprising the steps of (a) receiving a substrate comprising first and second structures produced using the lithographic process; (b) detecting scattered radiation while illuminating the first structure with radiation to obtain a first scatterometer signal; (c) detecting scattered radiation while illuminating the second structure with radiation to obtain a second scatterometer signal; (d) using the first and second scatterometer signals to determine an exposure dose value used to produce said first and second structures wherein the first structure has a first periodic characteristic with spatial characteristics and yet at least another second periodic characteristic with spatial characteristics designed to be affected by the exposure dose and the second structure has a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

According to an aspect, there is provided an inspection apparatus for determining exposure dose of a lithographic apparatus used in a lithographic process on a substrate, the inspection apparatus comprising: an illumination system configured to illuminate with radiation first and second structures produced using the lithographic process on the substrate; a detection system configured to detect scattered radiation arising from illumination of the first structures to obtain a first scatterometer signal and configured to detect scattered radiation arising from illumination of the second structures to obtain a second scatterometer signal; and a processor configured to use the first and second scatterometer signals to determine an exposure dose value used to produce the first structure, based on: the first structure having a first periodic characteristic with spatial characteristics and yet at least another second periodic characteristic with spatial characteristics designed to be affected by the exposure dose and the second structure having a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

According to an aspect, there is provided patterning device for determining exposure dose of a lithographic apparatus used in a lithographic process on a substrate, the patterning device comprising a target pattern comprising: a first sub-pattern configured to produce a first structure using the lithographic process, the first structure having structures with a periodic characteristic with spatial characteristics and yet another second periodic characteristic with a spatial characteristics designed to be affected by the exposure dose and a second sub-pattern configured to produce a second structure using the lithographic process, the second structures having a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

According to an aspect, there is provided a substrate for determining exposure dose of a lithographic apparatus used in a lithographic process on the substrate, the substrate comprising a target comprising: a first structure having at least a first periodic characteristic and yet another second periodic characteristic with a spatial characteristic designed to be affected by the exposure dose and a second structure having at least a first periodic characteristic and yet at least another second periodic characteristic with spatial characteristics designed to be affected by the exposure dose wherein the exposure dose affects the exposure dose affected spatial characteristics of the first and second structures in an essential different manner.

According to an aspect, there is provided a method of manufacturing devices wherein a device pattern is applied to a series of substrates using a lithographic process, the method including determining exposure dose of the lithographic apparatus using at least one of the substrates using a method according to the first aspect and controlling the lithographic process for later substrates in accordance with the result of the method of determining exposure dose.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 3A-3D show (a) a schematic diagram of a dark field scatterometer for use in measuring targets according to embodiments of the invention using a first pair of illumination apertures, (b) a detail of diffraction spectrum of a target grating for a given direction of illumination (c) a second pair of illumination apertures providing further illumination modes in using the scatterometer for diffraction based overlay measurements and (d) a third pair of illumination apertures combining the first and second pair of apertures, respectively.

Figure 4:
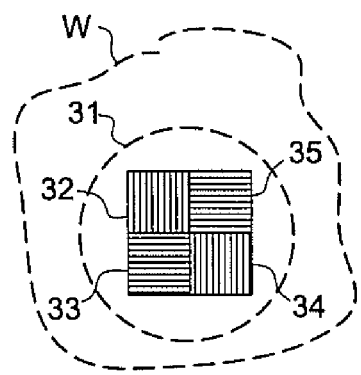

FIG. 4 depicts a known form of multiple grating target and an outline of a measurement spot on a substrate.

Figure 5:
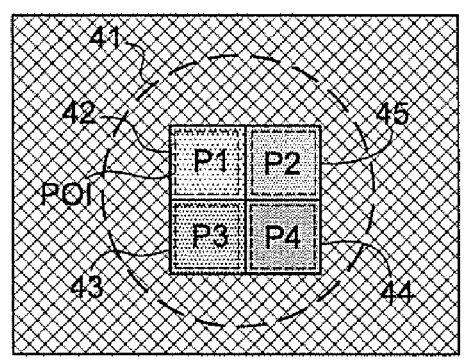

FIG. 5 depicts an image of the target of FIG. 4 obtained in the scatterometer of FIG. 3A.

FIGS. 6A-6C illustrate examples of targets according to an embodiment of the present invention.

FIGS. 7A-7C illustrate examples of targets according to an embodiment of the present invention, a graph that depicts intensity of a high order diffraction signal as a function of a parameter of the gratings, which is direct proportional to the exposure dose, and a graph that depicts intensity of a differential signal based on the high order diffraction signal, respectively.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
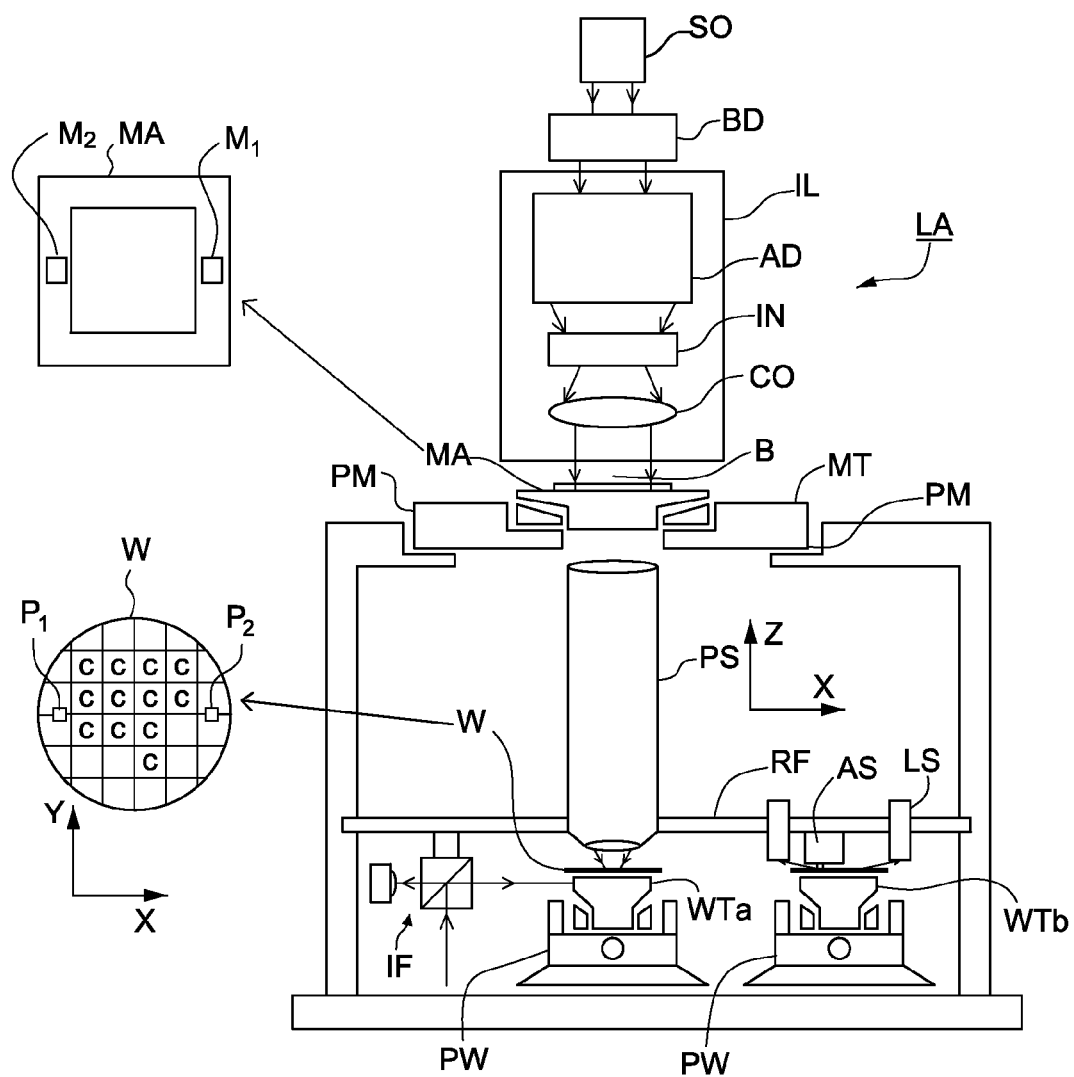
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
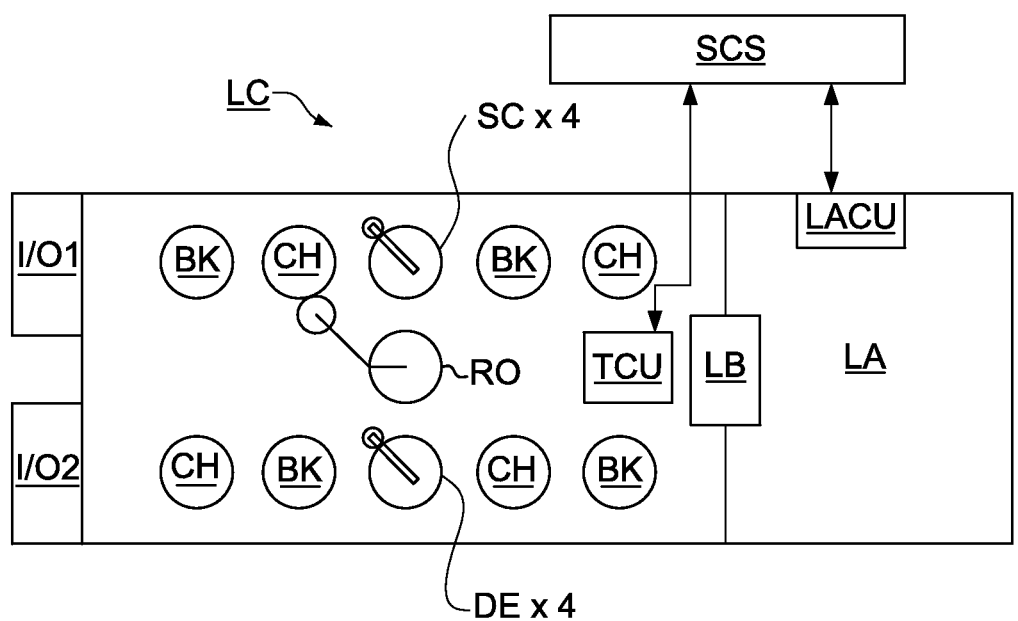
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Examples of dark-field metrology can be found in international patent applications WO 2009/078708 and WO 2009/106279 which documents are hereby incorporated by reference in their entirety. Further developments of the technique have been described in patent publications US20110027704A, US20110043791A and US20120123581A. The contents of all these applications are also incorporated herein by reference. US patent publication number US20110249247A discloses using measured scatterometer signals from focus-sensitive asymmetric target designs to measure defocus of a lithographic apparatus. The contents of that application are incorporated herein by reference. In such a method, asymmetric information, as available in the scatterometer pupil in the form of the difference between −1st and +1st diffraction order intensities, is used to infer scanner defocus from the measured scatterometer signals.

A dark field metrology apparatus suitable for use in embodiments of the invention is shown in FIG. 3A. A target grating T and diffracted rays are illustrated in more detail in FIG. 3B. The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3B, target grating T is placed with substrate W normal to the optical axis O of objective lens 16. A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled 1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image for an underfilled target may be used as an input for dose and focus metrology, in accordance with embodiments of the present invention.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3A are purely examples. In another embodiment of the invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3A) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial sight modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3C. The aperture plates 13N to 13W can be separately formed and interchanged, or they may be a single aperture plate which can be rotated by 90, 180 or 270 degrees. As mentioned already, the off-axis apertures illustrated in FIG. 3C could be provided in field stop 21 instead of in illumination aperture plate 13. In that case, the illumination would be on axis.

FIG. 3D shows a third pair of aperture plates that can be used to combine the illumination modes of the first and second pairs. Aperture plate 13NW has apertures at north and east, while aperture plate 13SE has apertures at south and west. Provided that cross-talk between these different diffraction signals is not too great, measurements of both X and Y gratings can be performed without changing the illumination mode.

FIG. 4 depicts a composite target formed on a substrate according to known practice. The composite target comprises four gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to defocus measurement, gratings 32 to 35 are themselves focus-sensitive gratings formed by asymmetric gratings that are patterned in layers of the semi-conductor device formed on substrate W. Gratings 32 to 35 may differ in their orientation, as shown, so as to diffract incoming radiation in X and Y directions. In one example, gratings 32 and 34 are X-direction gratings. Gratings 33 and 35 are Y-direction gratings. Separate images of these gratings can be identified in the image captured by sensor 23.

FIG. 5 shows an example of an image that may be formed on and detected by the sensor 23, using the target of FIG. 4 in the apparatus of FIG. 3A, using the aperture plates 13NW or 13SE from FIG. 3D. While the pupil plane image sensor 19 cannot resolve the different individual gratings 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process, such as focus, illustrated in application US20110027704A, which is incorporated by reference herein in its entirety.

A difficulty with the measurements using the scatterometer of FIG. 3A and targets illustrated in FIG. 4, with the corresponding images illustrated in FIG. 5, is that they are considered slow for the purpose of measuring exposure dose. Use of alternative equipment, such as CD-SEM, leads to similar extended measurement times.

Additionally, it is recognized that careful recipe setup is needed to overcome sensitivity of the metrology tools to various parameters affecting the measurement targets.

Additionally, it is also recognized that current exposure dose measurement techniques are using large metrology targets which are detrimental as said targets occupy substrate surface which would be used otherwise for semiconductor devices.

The present invention addresses above mentioned problems by providing a method to measure exposure dose using modulated targets. Said modulated targets contain gratings with a first pitch in one direction and a secondary pitch in an arbitrary direction. The periodic features corresponding to said secondary pitch are designed to have a shape which depends on the exposure dose. Said periodic features corresponding to said secondary pitch will create higher orders in the diffraction pattern which are proportional directly to the exposure dose. Considering two targets which have features designed to respond in a different manner to the exposure dose, one is able to extract the said exposure dose from the measured differential signal, differential signal which is based on the difference between the high order diffracted intensities from the two said targets.

The present invention addresses the above mentioned problems by providing a method of determining exposure dose of a lithographic apparatus used in a lithographic process on a substrate, the method comprising the steps:

(a) receiving a substrate comprising first and second structures produced using the lithographic process;

(b) detecting scattered radiation while illuminating the first structure with radiation to obtain a first scatterometer signal;

(c) detecting scattered radiation while illuminating the second structure with radiation to obtain a second scatterometer signal;

(d) using the first and second scatterometer signals to determine an exposure dose value used to produce said first and second structures wherein the first structure has a first periodic characteristic with spatial characteristics and yet at least another second periodic characteristic with spatial characteristics designed to be affected by the exposure dose and the second structure has a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner. Current invention further comprising using the lithographic process to produce a first structure on the substrate, the first structure having at least a first periodic characteristic and a second periodic characteristic with spatial characteristics designed to be affected by the exposure dose; and using the lithographic process to produce a second structure on the substrate, the second structure having at least a first periodic characteristic and a second periodic characteristic with spatial characteristic designed to be affected by the exposure dose wherein the exposure dose affects the exposure dose affected spatial characteristics of the first and second structures in a different manner.

The advantage of modulated targets is that said targets are suitable to be used in existing diffraction based scatterometers which leads to fast measurements decreasing therefore the time necessary to extract the exposure dose. The second pitch of the modulated target is superimposed on existing metrology targets which have a first pitch grating used for other measurements, for example overlay or focus which helps in reducing the areas on the wafer used for metrology. Another advantage is also the possibility to used smaller targets, as the method is suitable for dark field image scatterometry.

Different embodiments enabling fast exposure dose measurement using targets having a secondary pitch which is dose sensitive are described hereinafter.

FIGS. 6A-6C describes three different examples of targets which illustrate said concept of a modulated target. FIG. 6A depicts a periodic structure with a constant pitch between the gratings 601. FIG. 6B depicts another periodic structure whereby a second grating is introduced. The pitch of structure is in the same direction for both gratings, given by element 620. The elements 610 are similar gratings. Yet another example is given in FIG. 6C whereby the shape of each grating 630 is modified according to element 640. The periodic structure with elements 630 is periodic in a direction perpendicular on the elements 630. The structures 640 are also periodic but in a direction parallel with elements 630. For simplicity of the figure, they are not shown. In the example of FIG. 6C the pitch of elements 630 can be 100 nm whereas the pitch corresponding to features 640 is 600 nm. The gratings depicted in FIGS. 6A-6C can be produced using a lithographic process. The lithographic process is used to produce a first structure on the substrate, the first structure having at least a first periodic characteristic and a second periodic characteristic with spatial characteristics designed to be affected by the exposure dose; and using the lithographic process to produce a second structure on the substrate, the second structure having at least a first periodic characteristic and a second periodic characteristic with spatial characteristic designed to be affected by the exposure dose wherein the exposure dose affects the exposure dose affected spatial characteristics of the first and second structures in a different manner.

In an embodiment, the first periodic characteristics of the first and second structures are pitches of a metrology target containing gratings. The gratings depicted in FIGS. 6A-6C can form a metrology target, of the kind described in FIG. 4. The gratings depicted in FIGS. 6A-6C can also form a metrology target which can be used in a single layer.

In yet another embodiment, the second periodic characteristic of the first and second structure are pitches of a metrology target containing gratings. Moreover, the direction of the second periodic characteristics of the first and second structures is in a plane parallel with the plane where the first and second structures are. In one embodiment, which serves as an example, the direction of the second periodic characteristics of the first and second structures is substantially parallel with the direction of the first periodic characteristics of the first and second structures. In yet another embodiment, which also serves as an example, the direction of the second periodic characteristics of the first and second structures is substantially perpendicular to the direction of the first periodic characteristics of the first and second structures.

In another embodiment, the above mentioned steps of detecting scattered radiation while illuminating the first and second structures are performed using image-plane detection scatterometry. It is also recognized that the above mentioned steps of detecting scattered radiation while illuminating the first and second structures are performed using pupil-plane detection scatterometry. By modulating an existing periodic structure 630 of FIG. 6C with elements 640 having a different period, higher order are created in the diffracted signal. If one designs elements 640 to be sensitive to lithographic exposure parameters, such as exposure dose or exposure focus, measurement of the high order diffracted signal intensity would be an indicator of the effect of non-nominal dose or focus. Such measurement would contain the steps of detecting scattered radiation comprises separating the zeroth order scattered radiation from higher order scattered radiation and detecting the higher order scattered radiation to obtain each respective scatterometer signal.

FIGS. 7A-7C illustrates a method of measurement of exposure dose used in a lithographic apparatus. Using said lithographic apparatus, a grating containing elements 601 can be created, whereby elements 601 can be elements of the devices transferred into resist with the lithographic apparatus. Within the area covered by elements 601 which are similar to the device features, one can define two structures which contain embedded features 701 in FIG. 7A and 702 in FIG. 7A. In this particular example, the period of elements 701 and 702 is similar to elements 640 in FIG. 6C. Such period is perpendicular to the period of the elements 601. The pitch of elements 701 and 702 can be 600 nm. Elements 701 and 702 are designed to be sensitive to the exposure dose. The diffracted signal is measured on a first structure made of targets having elements 601 modulated with elements 701 and on a second structure made of targets having elements 601 modulated with elements 702. The measured higher order signal, represented in FIG. 7B by element 721 will be line 711 for the first structure represented in FIG. 7A and line 710 for the second structure represented in FIG. 7A. Elements 711 and 712 depict a different dependence on exposure dose of the measured high order diffracted signal intensity. Element 720 in FIG. 7B is the change in the critical dimension of the gratings and it is direct proportional to the exposure dose. In the actual implementation of this embodiment, element 720 will be the exposure dose. The method further comprises the extraction of a differential signal 722, which is the difference between signal 710 and 711. Differential signal 722 is also normalized to the sum of the intensities corresponding to the respective first and second measured scatterometer signal. In FIG. 7C, for each measured element 722, a corresponding value on elements 720 is found through relation 712, which leads to the extraction of the exposure dose with all the advantages mentioned above. The method uses the step of using the first and second scatterometer signals to determine an exposure dose value used to produce said first and second structures comprises using a difference between first and second measured intensities corresponding to the respective first and second measured scatterometer signals. Moreover, the step of using the first and second scatterometer signals to determine an exposure dose value used to produce said first and second structures comprises a normalization step and the normalization factor is the sum of the intensities corresponding to the respective first and second measured scatterometer signals. The second periodic characteristic of said first and second structures has a period of 600 nm.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the physical grating structures of the targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3A and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3A, is already in production and/or in use, the invention can be implemented by the provision of updated computer program products for causing a processor to perform the methods described herein and so calculate exposure dose and also defocus with reduced sensitivity to exposure dose. The program may optionally be arranged to control the optical system, substrate support and the like to perform the steps for measurement of a suitable plurality of target structures.

Further embodiments according to the invention are provided in below numbered clauses:

1. A method of determining exposure dose of a lithographic apparatus used in a lithographic process on a substrate, the method comprising the steps:

(a) receiving a substrate comprising first and second structures produced using the lithographic process;

(b) detecting scattered radiation while illuminating the first structure with radiation to obtain a first scatterometer signal;

(c) detecting scattered radiation while illuminating the second structure with radiation to obtain a second scatterometer signal;

(d) using the first and second scatterometer signals to determine an exposure dose value used to produce said first and second structures wherein the first structure has a first periodic characteristic with spatial characteristics and yet at least another second periodic characteristic with spatial characteristics designed to be affected by the exposure dose and the second structure has a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

2. The method of clause 1, further comprising: using the lithographic process to produce a first structure on the substrate, the first structure having at least a first periodic characteristic and a second periodic characteristic with spatial characteristics designed to be affected by the exposure dose; and using the lithographic process to produce a second structure on the substrate, the second structure having at least a first periodic characteristic and a second periodic characteristic with spatial characteristic designed to be affected by the exposure dose wherein the exposure dose affects the exposure dose affected spatial characteristics of the first and second structures in a different manner.

3. The method of clause 1 or clause 2, wherein the first periodic characteristics of the first and second structures are pitches of a metrology target containing gratings.

4. The method of any previous clause wherein the second periodic characteristic of the first and second structure are pitches of a metrology target containing gratings.

5. The method of any previous clause, wherein the direction of the second periodic characteristics of the first and second structures is in a plane parallel with the plane where the first and second structures are.

6. The method of clause 5, wherein the direction of the second periodic characteristics of the first and second structures is substantially parallel with the direction of the first periodic characteristics of the first and second structures.

7. The method of clause 5 wherein the direction of the second periodic characteristics of the first and second structures is substantially perpendicular to the direction of the first periodic characteristics of the first and second structures.

8. The method of any previous clause, wherein the steps of detecting scattered radiation while illuminating the first and second structures are performed using image-plane detection scatterometry.

9. The method of any previous clause, wherein the steps of detecting scattered radiation while illuminating the first and second structures are performed using pupil-plane detection scatterometry.

10. The method of any previous clause, wherein the steps of detecting scattered radiation comprises separating the zeroth order scattered radiation from higher order scattered radiation and detecting the higher order scattered radiation to obtain each respective scatterometer signal.

11. The method of any previous clause, wherein the step of using the first and second scatterometer signals to determine an exposure dose value used to produce said first and second structures comprises using a difference between first and second measured intensities corresponding to the respective first and second measured scatterometer signals.

12. The method of clause 11, wherein the step of using the first and second scatterometer signals to determine an exposure dose value used to produce said first and second structures comprises a normalization step.

13. The method of clause 12, wherein the normalization factor is the sum of the intensities corresponding to the respective first and second measured scatterometer signals.

14. The method of any previous clause, wherein the second periodic characteristic of said first and second structures has a period of 600 nm.

15. An inspection apparatus for determining exposure dose of a lithographic apparatus used in a lithographic process on a substrate, the inspection apparatus comprising:

an illumination system configured to illuminate with radiation first and second structures produced using the lithographic process on the substrate;

a detection system configured to detect scattered radiation arising from illumination of the first structures to obtain a first scatterometer signal and configured to detect scattered radiation arising from illumination of the second structures to obtain a second scatterometer signal; and a processor configured to use the first and second scatterometer signals to determine an exposure dose value used to produce the first structure, based on:

the first structure having a first periodic characteristic with spatial characteristics and yet at least another second periodic characteristic with spatial characteristics designed to be affected by the exposure dose and the second structure having a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

16. The inspection apparatus of clause 15, wherein the first periodic characteristics of the first and second structures are pitches of a metrology target containing gratings.

17. The inspection apparatus of clause 15, wherein the second periodic characteristics of the first and second structure are pitches of a metrology target containing gratings.

18. The inspection apparatus of clause 16 or 17, wherein the direction of the second periodic characteristics of the first and second structures is substantially parallel with the direction of the first periodic characteristics of the first and second structures.

19. The inspection apparatus of clause 16 or 17, wherein the direction of the second periodic characteristic of the first and second structures is substantially perpendicular to the direction of the first periodic characteristics of the first and second structures.

20. The inspection apparatus of any of the clauses 15 to 19, wherein the steps of detecting scattered radiation while illuminating the first and second structures are performed using image-plane detection scatterometry.

21. The inspection apparatus of any of the clauses 15 to 19, wherein the steps of detecting scattered radiation while illuminating the first and second structures are performed using pupil-plane detection scatterometry.

22. The inspection apparatus of clause 15, wherein the processor is configured to use the first and second scatterometer signals to determine an exposure dose value used to produce said first and second structures based on calculating the difference between first and second measure intensities corresponding to the respective first and second measured scatterometer signals.

23. The inspection apparatus of clause 22, wherein the step of using the first and second scatterometer signals to determine an exposure dose value to produce first and second structures comprises a normalization step.

24. The inspection apparatus of clause 23, wherein the normalization factor is the sum of the intensities corresponding to the respective first and second measured scatterometer signals.

25. The inspection apparatus of any of the clauses 15 to 24, wherein the detection system is configured to detect scattered radiation by separating zeroth order scattered radiation from any higher order scattered radiation and detecting the higher order scattered radiation to obtain each respective scatterometer signal.

26. A substrate for determining exposure dose of a lithographic apparatus used in a lithographic process on the substrate, the substrate comprising a target comprising:

a first structure having at least a first periodic characteristic and yet another second periodic characteristic with a spatial characteristic designed to be affected by the exposure dose and a second structure having at least a first periodic characteristic and yet at least another second periodic characteristic with spatial characteristics designed to be affected by the exposure dose wherein the exposure dose affects the exposure dose affected spatial characteristics of the first and second structures in a different manner.

27. The substrate of clause 26, wherein the first and second periodic characteristics of the first and second structures are pitches of a metrology target containing gratings.

28. A patterning device for determining exposure dose of a lithographic apparatus used in a lithographic process on a substrate, the patterning device comprising a target pattern comprising:

a first sub-pattern configured to produce a first structure using the lithographic process, the first structure having structures with a periodic characteristic with spatial characteristics and yet another second periodic characteristic with a spatial characteristics designed to be affected by the exposure dose and a second sub-pattern configured to produce a second structure using the lithographic process, the second structures having a first periodic characteristic with spatial characteristics and yet at least another second periodic characteristic with spatial characteristics designed to be affected by the exposure dose wherein the exposure dose affects the exposure dose affected spatial characteristics of the first and second structures in a different manner.

29. The patterning device of clause 28, wherein the first and second periodic characteristics of the first and second structures are pitches on a patterning device suitable to be used for forming on a substrate a metrology target containing gratings.

30. A method of manufacturing devices wherein a device pattern is applied to a series of substrates using a lithographic process, the method including determining exposure dose of the lithographic apparatus using at least one of the substrates using a method according to any of clauses 1 to 14, and controlling the lithographic process for later substrates in accordance with the result of the method of determining exposure dose.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of determining an exposure dose value of a lithographic apparatus used in a lithographic process on a substrate, the method comprising:
   detecting radiation scattered from first and second structures on the substrate, the first structure having a first periodic characteristic and a second periodic characteristic different from the first periodic characteristic and the second structure having a third periodic characteristic and a fourth periodic characteristic different from the third periodic characteristic;
   generating first and second scatterometer signals based on the scattered radiation detected from the first and second structures, respectively; and
   determining, based on the first and second scatterometer signals, the exposure dose value used to produce the first and second structures,
   wherein the exposure dose value affects the first and second structures in a different manner, and
   wherein the second periodic characteristic is superimposed on an existing structure to create the first structure.

2. The method of claim 1, wherein the first, second, third, and fourth periodic characteristics are pitches of a metrology target comprising gratings.

3. The method of claim 1, wherein directions of the second and fourth periodic characteristics are in a plane parallel with a plane where the first and second structures are located.

4. The method of claim 1, wherein a direction of the second or fourth periodic characteristic is substantially parallel with a direction of the first or third periodic characteristic, respectively.

5. The method of claim 1, wherein a direction of the second or fourth periodic characteristic is substantially perpendicular to a direction of the first or third periodic characteristic, respectively.

6. The method of claim 1, wherein the determining of the exposure dose value is based on a difference between first and second measured intensities corresponding to the first and second scatterometer signals, respectively.

7. The method of claim 1, wherein the determining of the exposure dose value comprises a normalization step.

8. The method of claim 7, wherein the normalization step comprises using a normalization factor that is a sum of first and second measured intensities corresponding to the first and second scatterometer signals, respectively.

9. An inspection apparatus for determining an exposure dose value of a lithographic apparatus used in a lithographic process on a substrate, the inspection apparatus comprising:
   an illumination system configured to illuminate with radiation first and second structures produced on the substrate using the lithographic process, wherein:
      the first structure comprises first and second periodic characteristics that are different from each other,
      the second structure comprises third and fourth periodic characteristics that are different from each other,
      the exposure dose value affects the first and second structures in a different manner, and the second periodic characteristic is superimposed on an existing structure to create the first structure;

a detection system configured to:
   detect scattered radiation arising from illumination of the first and second structures, and
   generate first and second scatterometer signals based on the scattered radiation detected from the first and second structures, respectively; and
a processor configured to determine the exposure dose value used to produce the first and second structures based on the first and second scatterometer signals.

10. The inspection apparatus of claim 9, wherein the first, second, third, and fourth periodic characteristics are pitches of a metrology target comprising gratings.

11. The inspection apparatus of claim 9, wherein a direction of the second or fourth periodic characteristic is substantially parallel with a direction of the first or third periodic characteristic, respectively.

12. The inspection apparatus of claim 9, wherein a direction of the second or fourth periodic characteristic is substantially perpendicular to a direction of the first or third periodic characteristic, respectively.

13. The inspection apparatus of claim 9, wherein the processor is configured to determine the exposure dose value based on a difference between first and second measured intensities corresponding to the first and second scatterometer signals, respectively.

14. The inspection apparatus of claim 9, wherein the processor is configured to determine the exposure dose value based on a normalization step.

15. The inspection apparatus of claim 9, wherein the processor is configured to determine the exposure dose value based on a normalization factor that is a sum of first and second measured intensities corresponding to the first and second scatterometer signals, respectively.

16. The inspection apparatus of claim 9, wherein the detection system is configured to:
   separate zeroth order scattered radiation from a higher order scattered radiation; and
   detect the higher order scattered radiation to generate the first and second scatterometer signals.

17. A substrate for determining an exposure dose value of a lithographic apparatus used in a lithographic process on the substrate, the substrate comprising a target comprising:
   a first structure comprising first and second periodic characteristics that are different from each other; and
   a second structure comprising third and fourth periodic characteristics that are different from each other,
   wherein the exposure dose value affects first and second structures in a different manner, and
   wherein the second periodic characteristic is superimposed on an existing structure to create the first structure.

18. A patterning device for determining an exposure dose value of a lithographic apparatus used in a lithographic process on a substrate, the patterning device comprising a target pattern comprising:
   a first sub-pattern configured to produce a first structure using the lithographic process, the first structure comprising first and second periodic characteristics that are different from each other; and
   a second sub-pattern configured to produce a second structure using the lithographic process, the second structure comprising third and fourth periodic characteristics that are different from each other,
   wherein the exposure dose value affects the first and second structures in a different manner, and
   wherein the second periodic characteristic is superimposed on an existing structure to create the first structure.

19. A device manufacturing method comprising:
applying a device pattern to a series of substrates using a lithographic process;
determining an exposure dose value of a lithographic apparatus using at least one substrate from the series of substrates, the determining of the exposure dose value comprising:
   detecting radiation scattered from first and second structures on the substrate, the first structure having first and second periodic characteristics that are different from each other and the second structure having third and fourth periodic characteristics that are different from each other,
   generating first and second scatterometer signals based on the scattered radiation detected from the first and second structures, respectively, and
   determining, based on the first and second scatterometer signals, the exposure dose value used to produce the first and second structures,
   wherein the exposure dose value affects the first and second structures in a different manner, and
   wherein the second periodic characteristic is superimposed on an existing structure to create the first structure; and
controlling the lithographic process for other substrates from the series of substrates based on the determined exposure dose value.

* * * * *